United States Patent [19]
Tran

[11] Patent Number: 4,842,598
[45] Date of Patent: Jun. 27, 1989

[54] THERAPEUTIC AGENT DELIVERY SYSTEM AND METHOD
[75] Inventor: Loi H. Tran, Wheaton, Ill.
[73] Assignee: Controlled Release Technologies, Inc., Batavia, Ill.
[21] Appl. No.: 137,761
[22] Filed: Dec. 24, 1987

Related U.S. Application Data
[62] Division of Ser. No. 679,128, Dec. 6, 1984, Pat. No. 4,715,850.
[51] Int. Cl.⁴ .............................................. A61M 5/00
[52] U.S. Cl. .................................. 604/891.1; 604/131; 204/130
[58] Field of Search ................... 604/82, 83, 86, 87, 604/93, 126, 891.1, 131; 204/130, 131

[56] References Cited
U.S. PATENT DOCUMENTS
| | | | |
|---|---|---|---|
| 4,140,121 | 2/1979 | Kühl et al. | 604/891.1 |
| 4,436,094 | 3/1984 | Cerami | 128/635 |
| 4,540,403 | 9/1985 | Theeuwes | 604/85 |
| 4,639,244 | 1/1987 | Rizk et al. | 604/891.1 |

Primary Examiner—Stephen C. Pellegrino
Attorney, Agent, or Firm—Olson & Hierl

[57] ABSTRACT

A method and apparatus for controllably administering a therapeutic agent to a patient is disclosed. The method and apparatus uses an electromotive force between an anode and a cathode to cause the therapeutic agent to migrate through a semipermeable membrane. The therapeutic agent is then delivered to the patient.

6 Claims, 5 Drawing Sheets

FIG_2_

FIG_3_

FIG-4

PLOT OF MILLIGRAMS OF DOXORUBICIN VS TIME

FIG-5

PLOT OF PEAK AREA OF DOXORUBICIN VS CURRENT INTENSITY

FIG. 6

PLOT OF MILLIGRAMS OF LIDOCAINE VS TIME

FIG. 7

PLOT OF PEAK AREA OF LIDOCAINE VS CURRENT INTENSITY

FIG. 8

PLOT OF MILLIGRAMS OF CLONIDINE VS TIME

FIG. 9

PLOT OF PEAK AREA VS CURRENT INTENSITY (CLONIDINE)

THERAPEUTIC AGENT DELIVERY SYSTEM AND METHOD

This is a division of application Ser. No. 679,128, filed Dec. 6, 1984, now Pat. No. 4,715,850, granted Dec. 29, 1987.

TECHNICAL FIELD OF THE INVENTION

The present invention relates to systems and methods for administering a therapeutic agent to a patient by means of an electromotive force between electrodes.

BACKGROUND OF THE INVENTION

It is quite common to administer a drug to a patient over time by first diluting the drug in a liquid vehicle such as saline. Generally, the drug is mixed with the liquid vehicle, and the resulting solution is then administered intravenously to the patient. However, once mixed, the concentration of the drug in the solution remains relatively constant and only the administration rate of the solution can be adjusted.

To allow changes in drug concentrations, devices that mix the drug with the liquid vehicle have been developed. These devices use roller clamps to separately control the drip rates of the drug and liquid vehicle into a mixing chamber. Once the roller clamps are set, the mixing ratio remains the same until someone changes the settings. Even this type of system does not allow for the periodic automatic administration of a bolus of drug.

Other devices provide for the sequential administration of a drug followed by a physiologically tolerable liquid carrier such as saline. Such systems provide for the automatic switching to the saline after the drug has been administered. Unfortunately, none of these devices provide for timing or variable control of the administration of the drug to the patient.

It is sometimes desirable to administer a bolus of a particular drug at given times to the patient. Present devices for such administration rely on electrical timer systems that operate mechanical valves. The rates and time of drug administration are set in the device, and the valves are opened and closed automatically. However, such devices are relatively complicated and rely on the operation of a mechanical valve having the inherent disadvantage of possible failure through valve malfunction.

What is needed is a system and method for delivering a therapeutic agent to a patient which is easily adjustable without the need of mechanical means. Such a device should allow for the easy control of administration rates as well as times of administration. The present invention meets these desires.

SUMMARY OF THE INVENTION

The present invention is a system and method for delivering a therapeutic agent to a patient by use of an electromotive force between an anode and a cathode. Suitable therapeutic agents include active agents such as drugs or hormones, or active agents coupled to an appropriate carrier. Either the active agent or the carrier is in an ionic form such as a pharmaceutically acceptable salt. For example, such a salt can be represented by the formula $RY^+X^-$ wherein $RY^+$ includes a cationic (positively charged) group such as $RNH_3^+$, and $X^-$ is an anionic (negatively charged group such as $Cl^-$ or $Br^-$.

A housing means defines a cavity which is divided by a semipermeable membrane to define a donor chamber adapted to receive the therapeutic agent and a receiving chamber adapted to receive the therapeutic agent from the donor chamber through the membrane. Two electrodes, an anode and cathode, are in fluid communication with the cavity such as by being exposed within the cavity. When an electromotive force of a sufficient amount is applied between electrodes, at least a portion of the therapeutic agent migrates through the semipermeable membrane to be delivered to the patient. The rate of therapeutic agent delivery is a function of the current between the electrodes.

In one preferred embodiment of the invention, one electrode is in fluid communication with the donor chamber and the other electrode is placed on the other side of the semipermeable membrane in fluid communication with the receiving chamber. The electrode in fluid communication with the donor chamber will have the same charge as the ionized therapeutic agent. For a hydrochloride salt, the ionized therapeutic agent has a positive charge and this electrode is an anode.

The semipermeable membrane is ion-selective to allow the charged therapeutic agent, but not its oppositely charged corresponding ion to pass through the membrane. In the case of a positively charged therapeutic agent such as $RY^+$, the membrane allows the passage of cations but is substantially impermeable to anions such as chloride ions. Even though the therapeutic agent ions could diffuse through the semipermeable membrane when there is no electromotive force between the electrodes, there is no net flow of agent because of the need to maintain an electrochemical balance between the two chambers. Thus, if an excess of the cationic therapeutic agent were to diffuse through the membrane, the donor chamber would have a net negative charge and the agent would be drawn back to maintain the necessary electrochemical balance. The anionic chloride ions can not also pass through the membrane with the agent.

However, when an electromotive force or charge is placed between the anode and the cathode, the ionized therapeutic agent migrates through the semipermeable membrane. The externally applied charge negates the necessity for maintaining an electrical balance between the ions in the two chambers and provides a driving force for the cationic agent toward the cathode in the receiving chamber.

After the therapeutic agent enters the receiving chamber, it can be delivered to the patient by appropriate delivery means. One preferred form of delivery is to pass a liquid vehicle such as of saline through the receiving chamber to mix with the therapeutic agent and deliver the mixture to the patient intravenously.

In another preferred embodiment of the present invention, both the anode and cathode are in fluid communication with the donor chamber. The semipermeable membrane in this instance is substantially impermeable to the ionic form of the therapeutic agent, but is permeable to the non-ionic form of the therapeutic agent. One example of such a membrane is a hydrophobic membrane. The therapeutic agent is placed within the donor chamber in its ionic form where it is retained by the membrane. When an electromotive force is placed between the anode and cathode, the therapeutic agent changes from its ionic form to a non-ionic form which then passes through the membrane to be administered to the patient. In the example given above, $RY^+X^-$ is converted to RY, with $X^-$ combining with another ion such as silver $Ag^+$ from an anode.

Both embodiments discussed above permit easy control of the rate and amount of therapeutic agent which is administered to the patient. The rate of administration is a function of the current between the anode and the cathode while the total amount administered is a function of the rate and time that an electromotive force is applied between the anode and the cathode. This provides for easy control without the necessity of a complicated valve mechanism.

Because an electrical current operates the present invention, electrical control is easily accomplished by an appropriate control means such as a microprocessor associated with power source means such as a battery. The system also has the inherent advantage that should there be any form of power interruption, there is no longer a potential between the electrodes and no therapeutic agent is administered to the patient.

Numerous other advantages and features of the present invention will become readily apparent to those skilled in the art from the following detailed description of the preferred embodiments of the invention, the drawings, and the claims.

DETAILED DESCRIPTION OF THE PREFERRED EMBODIMENTS

While this invention can be embodied in many different forms, there are shown in the drawings and described in detail, preferred embodiments of the present invention. The present disclosure is an exemplification of the principles of the invention and is not intended to limit the invention to the embodiments illustrated.

The present invention is a method and system for administering a therapeutic agent to a patient. The therapeutic agent can be almost any active agent such as a drug or hormone which can exist in an ionized form or any active agent which can be coupled to a carrier which is ionizable.

Either the active agent or the carrier is in an ionic form. One such compound is a pharmaceutically acceptable salt. Such a salt can be represented by the formula $RY^+X^-$ wherein $RY^+$ includes a cationic group such as $NH_3^+$, $NH_2^+$ or $NH^+$ and $X^-$ is an anion such as $Cl^-$ or $Br^-$. Also possible are compounds having the general formula $RY^-X^+$, such as where $Y^-$ is a carboxyl group, a sulfonate group, barbital (5,5-diethyl barbituric acid), or a phosphamide, and $X^+$ is a physiologically tolerable cation such as sodium, potassium, calcium or magnesium. In either case, R represents the remainder of the active agent or active agent-carrier combination. Generally, the small anion or cation (depending on the formula for the therapeutic agent either $X^-$ or $X^+$) will not be delivered to the patient. The portion represented by $RY^+$ or $RY^-$ is the active agent or active agent coupled to a carrier and is considered the therapeutic agent which is delivered to the patient. It is this portion which carries the active agent that has the therapeutic effect.

The therapeutic agent is placed within a donor chamber in its ionic form. The donor chamber is defined in part by a semipermeable membrane. When an electromotive force above a certain minimum amount (which varies depending on the agent and membrane) is placed between an anode and a cathode, the therapeutic agent migrates through the semipermeable membrane to be delivered to the patient.

Figure 1:
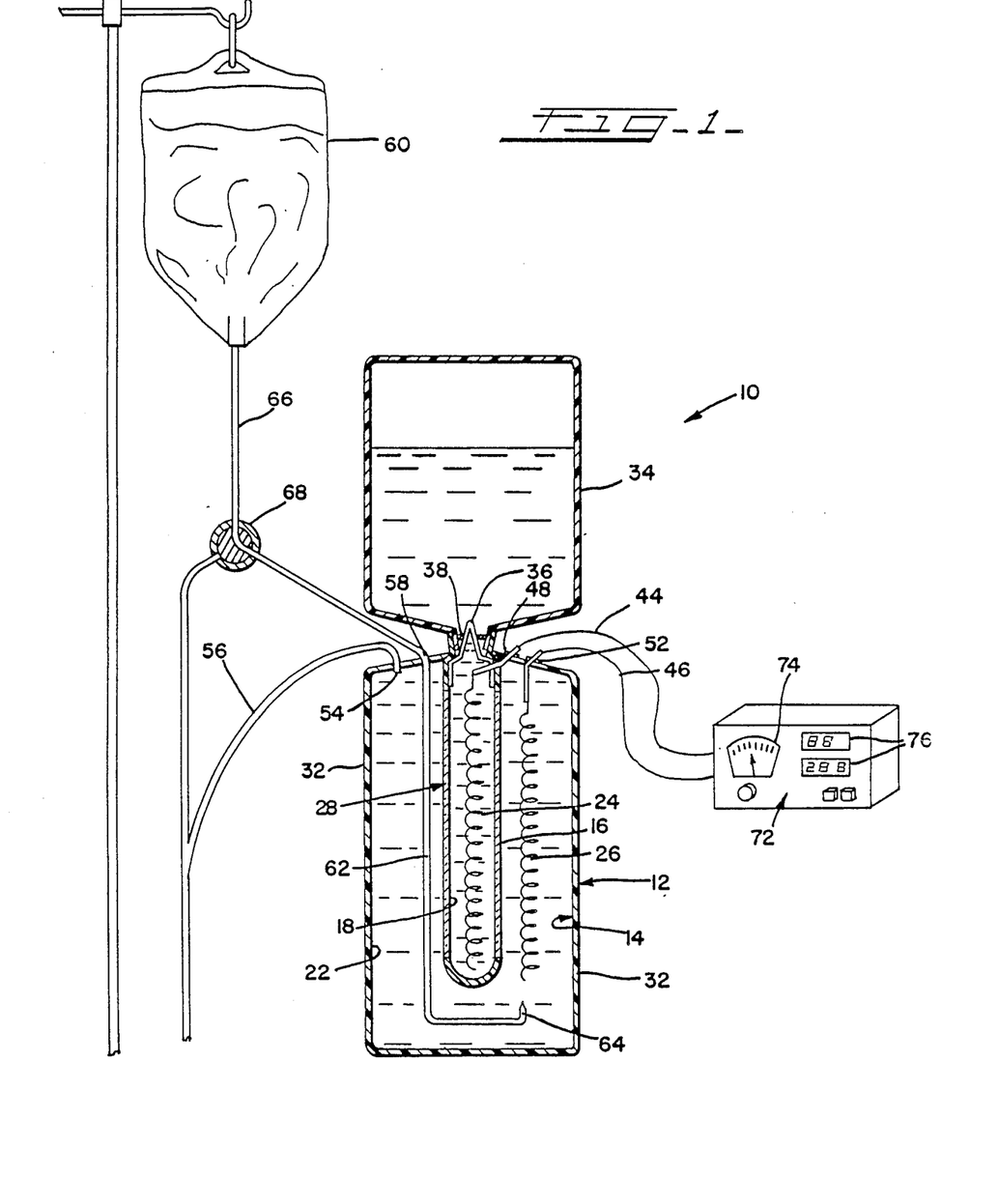
FIG. 1 is an elevational view, partly in section, of an embodiment of the present invention showing a donor chamber generally located within the receiving chamber together with means for delivering the therapeutic agent to a patient.

Referring to the first embodiment in FIG. 1, a device 10 of the present invention is shown with a housing means 12 defining a cavity 14 divided by a semipermeable membrane 16 into a donor chamber 18 and a receiving chamber 22. The donor chamber 18 is adapted to hold the therapeutic agent while the receiving chamber 22 is adapted to receive the therapeutic agent from the donor chamber through the membrane 16.

The housing means 12 includes a first housing 28 which defines the donor chamber 18 and a second housing 32 which defines the receiving chamber 22. As shown, the donor chamber 18 is separated from the receiving chamber 22 by the semipermeable membrane 16. The membrane 16 can be any suitable shape such as a sheet or as shown in FIG. 1, a hollow tube about 1.75 centimeters in diameter. The semipermeable membrane 16 can be considered as part of the structure which defines both the donor chamber 18 and the receiving chamber 22.

The semipermeable membrane 16 is permeable to the ionized therapeutic agent, but is substantially impermeable to an oppositely charged ion. In the case of a positively charged therapeutic agent, the membrane 16 permits the passage of cations, but substantially prevents the passage of anions. The membrane 16 can be made of a microporous material having a pore size less than about 0.22 micrometers. Suitable materials for the membrane include anionic polymers such as perfluorosulfonic acid polymers, carboxylic acid polymers such as poly(sodium methacrylate), and phosphoric acid polymers such as poly(vinyl sodium phosphonate). One particularly preferred polymer is a perfluorosulfonic acid polymer having internal sulfonic acid groups sold by Cole-Parmer of Chicago, Ill. under the trademark Spectra/Por Ion Selective Membrane. Other suitable membranes include a cation exchange membrane sold by Asahi Glass & Co. under the trademark Selemion CSV.

Where the therapeutic agent is negatively ionized such as by ionizing a carboxyl or sulfonate group, the membrane should be permeable to anions and substantially impermeable to cations. Such membranes include: ammonium polymers; quaternary ammonium polymers such as polypyrazine, poly(vinyl trimethyl ammonium chloride), poly(N-methyl vinyl pyridinium chloride), poly(diallyl dimethyl ammonium chloride), and benzalkonium chloride polymers such as available from Rohm and Haas of Philadelphia, Pa. under the trademark Hyamin 1622. See generally, Hoover *J. Macromolecular Sci.* A4, p. 1327 (1970).

A membrane is considered to be ion selective if it has a higher diffusion rate for one type of ion as opposed to another. Thus, in the case of an anionic polymer, it is permeable to cations in that it allows cations to pass through the pores of the membrane, but is substantially impermeable to anions in that it substantially prevents the passage of anions. It should be kept in mind that no membrane is perfect and the passage of a certain small amount of anions is acceptable.

The device 10 also includes two electrodes, a first electrode 24 in fluid communication with the donor chamber 18 and a second electrode 26 in fluid communication with the receiving chamber 22. The electrodes are most easily placed in fluid communication with their respective chambers by being exposed within their respective chambers. In the case of a negatively ionized therapeutic agent, the first electrode 24 is a cathode while the second electrode 26 is an anode. However, for ease of description, the more common case of a positively charged ionized therapeutic agent will be given in which case the first electrode 24 is an anode and the second electrode 26 is a cathode.

The electrodes 24 and 26 can be made of any suitable material which preferably does not chemically react with either the therapeutic agent or any liquid vehicle within the system such as saline. Suitable electrode materials include platinum, silver, carbon and gold with silver being particularly preferred in implantable devices to avoid the production of chlorine gas by reacting the newly migrated silver ions with the excess chlorine ions to form silver chloride. As shown, the electrodes 24 and 26 are wire electrodes which are coiled to save space. Other configurations of electrodes are also possible such as flat ribbon electrodes having a high surface area. Leads 44 and 46 for the electrodes 24 and 26 are provided with appropriate seal means 48 and 52 as they enter their respective housing 28 and 32. The electrodes preferably having a surface area of about 0.50 to about 1.2 square centimeters.

In the embodiment shown in FIG. 1, the portion of the donor chamber 18 defined by the semipermeable membrane 16 is located within the receiving chamber 22. This allows for a maximizing of the surface area of the semipermeable membrane 16 between the two chambers while minimizing the overall size of the device.

A removable drug reservoir 34 can also be provided in fluid communication with the first housing 28. It is preferred that the drug reservoir 34 be elevated relative to the first housing 28 so that gravity drives the therapeutic agent into the donor chamber 18 to replace that agent which has passed through the semipermeable membrane 16 and has been administered to the patient.

As shown in FIG. 1, the first housing 28 is preferable provided with a spiked cannula 36 which pierces a septum 38 on the drug reservoir 34 as the drug reservoir is mounted on the first housing 28. This simplifies use since different types of therapeutic agents may be stored in replaceable drug reservoirs 34 and supplied as needed. This also simplifies refilling of the donor chamber 18 as the therapeutic agent is administered to the patient.

The first housing 28, second housing 32, and refillable drug reservoir 34 can be made of any suitable medical grade material. Such materials include glass, polypropylene, polyethylene, polycarbonate and polystyrene.

Delivery means for delivering the therapeutic agent from the receiving chamber 22 to the patient are also provided. Such delivery means can be as simple as an outlet 54 mounted on the second housing 32 in fluid communication with the receiving chamber 22. The therapeutic agent which passes through the membrane 16 into the receiving chamber 22 can then be delivered through the outlet 54 to the patient such as by means of an appropriate flexible tubing 56. The tubing 56 can be attached to a needle or catheter (not shown) to deliver the drug intravenously.

As shown in FIG. 1, the delivery means preferably also includes an inlet 58 mounted on the first container 32 in fluid communication with the receiving chamber 22. The inlet 58 is preferably connected to a conduit 62 which extends into the receiving chamber 22 and has an opening 64 which is spaced from the outlet 54 such that the flow of liquid vehicle from the inlet to the outlet dynamically mixes with the therapeutic agent in the receiving chamber 22 before delivery to the patient. The inlet 54 can be connected to an appropriate container 60 of a physiologically tolerable liquid vehicle such as saline by appropriate tubing 66. A three-way valve 68 can also be provided to either direct the flow of the liquid vehicle through the device 1 or to bypass the device and deliver the liquid vehicle directly to the patient.

As shown, the electrodes 24 and 46 are connected by leads 44 and 46 to an operating unit 72 including power source means and control means. The power source means provides a direct current from either a battery or includes appropriate means for reducing the power coming from a wall outlet and also converting it to DC power. The minimum amount of electromotive force varies depending on the therapeutic agent and membrane being used. In the case of a perfluorosulfonic acid polymer as described above, a minimum voltage of about 0.3 to about 0.4 volts is needed to drive a therapeutic agent such as doxorubicin hydrochloride through the membrane. The preferred operating voltage range of the device is from about 3 volts to about 6 volts, direct current.

The control means regulates the operation of the power source and can include an appropriate timing circuit that can be set to administer the therapeutic agent for a given amount of time, to administer a certain amount of therapeutic agent at regular periodic intervals, or to even alter the amount of therapeutic agent which is given at different times.

To a certain extent, the control means can also allow the patient to control the administration of the therapeutic agent. Thus, the patient would be able to receive a pain reducing agent when necessary, but the control means would provide an override to prevent the patient from overmedicating.

As shown on the operating unit 72 in FIG. 1, an ammeter 74 forming part of the power source means indicates the delivery rate of the therapeutic agent. As discussed in more detail below, the rate of therapeutic agent delivery is substantially a linear function of the current between the anode and cathode. As also shown on the operating unit 72, indicators 76 for a timing circuit form part of the control means.

Figure 2:
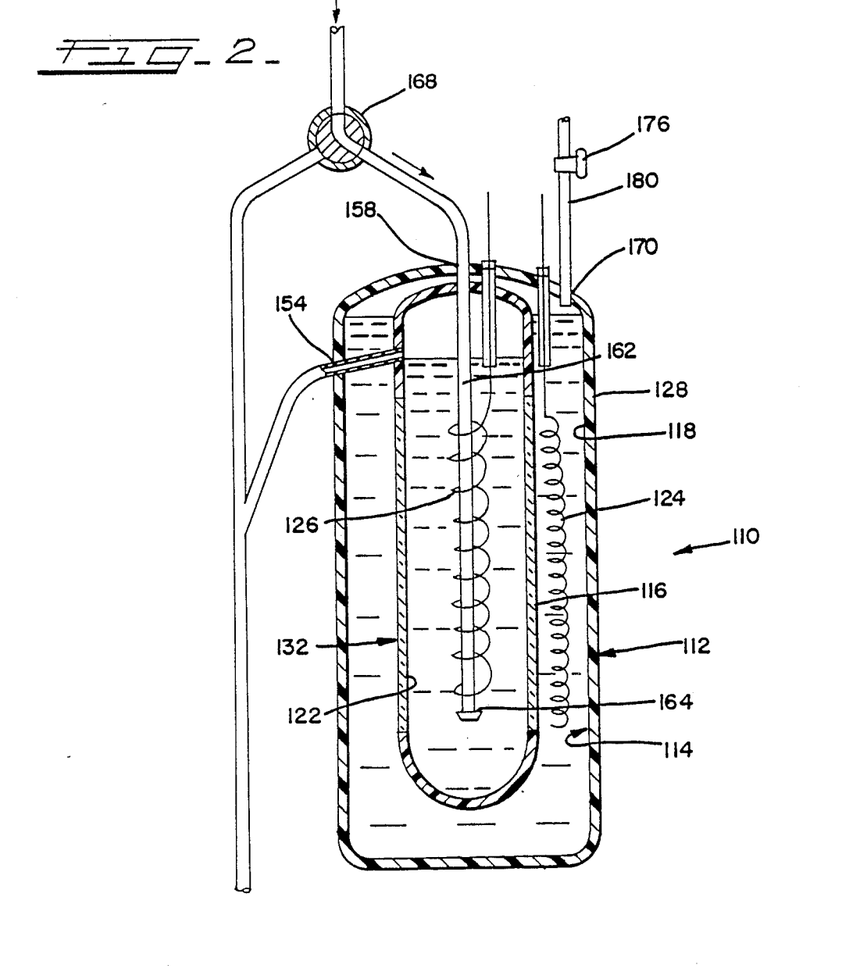
FIG. 2 is an alternative embodiment of the present invention in which the receiving chamber is located generally within the donor chamber.

Referring to FIG. 2, an alternative embodiment for a device 110 of the present invention is shown. As before, the device 110 includes a housing means 112 defining a cavity 114 and having a first housing 128 defining a donor chamber 118 and a second housing 132 defining a receiving chamber 122. Membrane 116 separates the two chambers. However, the second housing 132 is located within the first housing 128, the reverse of the device 10 shown in FIG. 1. As shown, the two housings 128 and 132 are substantially cylindrical and coaxial.

The first electrode 124 and the second electrode 126 are substantially as before. The delivery means includes inlet 158, conduit 162 and outlet 154 and three-way valve 168 which operate substantially as in FIG. 1. The opening 164 of the conduit 162 is provided with a flow directing means to provide for more efficient mixing of the physiologically tolerable liquid with the drug entering the receiving chamber 122.

The device 110 shown in FIG. 2 is also provided with a port 170 which can be connected by a tube 180 to a reservoir of therapeutic agent. Valve means 176 can be provided to regulate the flow of therapeutic agent into the donor chamber 118.

In operation of the devices 10 and 110, the therapeutic agent is placed within the donor chamber 18 in its ionic form such as a hydrochloride salt. Generally, the agent is dispersed in a physiologically tolerable dilutent such as saline. When it is desired to administer the therapeutic agent to the patient, an electromotive force is placed between the electrodes 24 and 26 such that the therapeutic agent migrates through the semipermeable membrane 26. Where electrode 26 is a cathode, a positively charged therapeutic agent will be driven through the semipermeable membrane 16 by the negative attraction of the electrode or cathode 26. The corresponding anode 24, if made of silver, will be ionized to become silver ions which react with the chloride ions to form silver chloride. The therapeutic agent which then arrives in the receiving chamber 22 can be taken up by the physiologically tolerable liquid vehicle flowing from the inlet 58 through the receiving chamber 22 and out through the outlet 54 to the patient.

The liquid vehicle preferably includes ions which correspond to those ions which do not pass through the membrane. In the case of a hydrochloride salt, the liquid vehicle includes chloride ions. Such a liquid vehicle is saline.

Figure 3:
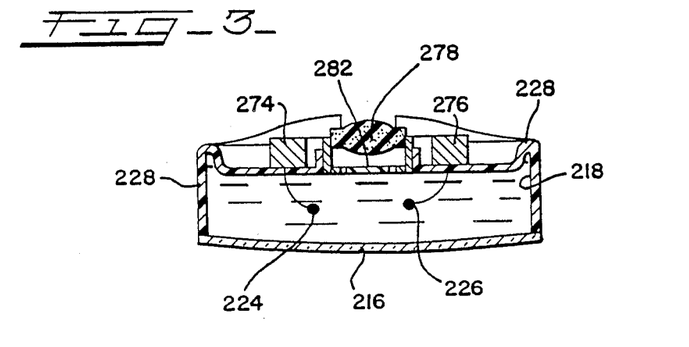
FIG. 3 is a still further alternative embodiment of the present invention having two electrodes located within a donor chamber.

A still further alternative design for a device 210 according to the present invention is shown in FIG. 3. In this embodiment, both anode 224 and cathode 226 are located within donor chamber 218 which is defined by housing 228 which retains semipermeable membrane 216. The semipermeable membrane 216 is substantially impermeable to the ionic form of the therapeutic agent, but permeable to the non-ionic form of the therapeutic agent.

The membrane 216 can be made of a hydrophobic material such as silicone elastomers consisting of dimethyl and methylvinyl siloxane copolymers commercially available from Dow Chemical under the trademark Silastic. Other suitable membranes include Teflon TFE membranes (trademark of du Pont de Nemours & Co.), a styrene ethylene/butylene, styrene block copolymer with polydimethylsiloxane available under the trademark C-Flex from Concept Polymer Technologies and a polytetrafluoroethylene available under the trademark Gore-Tex from W. L. Gore & Associates, Inc.

In the embodiment shown in FIG. 3, the power source means, in this case a battery 274 and the control means shown as a microprocessor 276 are mounted on the housing 228 to permit implantation of the entire device 210. The housing 228 and membrane 216 are also adapted for implantation into a living patient's body such as in the abdomen. A septum 278 and needle stop 282 are also provided to permit the supply of therapeutic agent to the donor chamber 218. When the device 210 is implanted, its supply of agent can be replenished through the patient's skin by a needle which extends through the septum 278.

In operation, the therapeutic agent is placed within the donor chamber 218 in its ionic form. The membrane 216 being hydrophobic resists the passage of ions. When an electromotive force is placed between the anode 224 and cathode 226, a current flows between them and the therapeutic agent is reduced to its non-ionic form. In its non-ionic form, the therapeutic agent can pass through the semipermeable membrane 216.

Since the therapeutic agent leaving the semipermeable membrane 216 is in a non-ionic form, it should be of a type which remains soluble in its non-ionic form. Such therapeutic agents include hormones and the drugs phenobarbital sodium and doxorubicin.

The therapeutic agent is preferably an ionizable drug which can be supplied as a pharmaceutically acceptable salt. The term "pharmaceutically acceptable salt" refers to the non-toxic alkali metal, alkaline earth metal and ammonium salts commonly used in the pharmaceutical industry including the sodium, potassium, lithium, calcium, magnesium, and ammonium salts and the like which are prepared by methods well known in the art. The term also includes non-toxic acid addition salts which are generally prepared by reacting the compounds of this invention with a suitable organic or inorganic acid. Representative salts include the hydrochloride, hydrobromide, sulfate, bisulfate, sulfonate, acetate, oxalate, valerate, oleate, laurate, borate, benzoate, lactate, phosphate, tosylate, citrate, barbital, maleate, fumarate, succinate, tartrate, and the like.

A wide range of drugs are available as pharmaceutically acceptable salts, and particularly are often available as hydrochloride salts. These include doxorubicin hydrochloride, clonidine hydrochloride, lidocaine hydrochloride, naloxone hydrochloride, nalorphine hydrochloride, morphine hydrochloride, morphine sulfate U.S.P., and bretylium tosylate. In addition, simple compounds such as used to provide electrolytes to a patient including potassium chloride and ammonium chloride can also be administered by the present invention.

Where the drug or hormone cannot be placed in an ionic form, or it is not desirable to place the drug or hormone in an ionic form, the therapeutic agent can include the drug or hormone coupled to an appropriate carrier which does have an ionic form. This is particularly useful for hormones such as insulin. Such appropriate carriers include the pyridine compounds. These compounds include a heterocyclic ring having a nitrogen which can form a quaternary amine salt when oxidized. See generally, Eisner et al., *The Chemistry of Dihydropyridines*, Chemical Reviews 72:1–42 (1972). such pyridinium salt-drug compounds have the general formula of:

wherein $R_1$ is generally a lower alkyl group ($C_1$–$C_4$) such as methyl or ethyl, D is an active agent such as a drug or hormone, $R_2$ is a coupling agent for linking the salt to the active agent D, such as $CH_2O$, COO, or $CH=NO$, and $X^-$ is an anion. For example, where the drug has an amine group that is used to couple it with the carrier, the coupling agent $R_2$ is usually COO to form a carbodiimide coupling. Pyridine can be reacted with an alkyl halide such as methyl chloride to form the quaternary ammonium salt desired such as N-methyl-pyridinium chloride. See for example, Bodor et al. *Journal of Pharmaceutical Sciences* 67:685–687 (1978) and Bodor et al. *Science,* 214:1370–1372 (1981). See also U.S. Pat. Nos. 3,929,813 and 3,962,447 to Higuchi et al., all incorporated by reference.

One suitable carrier 1-methylpyridinium-2-aldoxime chloride also known as 2-PAM chloride can be used in its cloride salt form and coupled to an active agent D as shown below.

It should be understood that numerous other compounds can be used as carriers, the primary criteria being the existance of an ionic form and being physiologically tolerable.

EXAMPLE 1

This example shows the controlled release of doxorubicin hydrochloride. A perfluorosulfonic acid polymer membrane obtained from Cole-Parmer under the trademark Spectra/POR was used as the semipermeable membrane. The membrane was 42 millimeters in diameter and had a filtration area which was exposed to the donor and receiving chambers of 10.5 square centimeters. The donor chamber had a volume of 140 cubic centimeters and the receiving chamber had a volume of 37.4 cubic centimeters.

The anode was a silver wire 1.5 millimeters in diameter, 18.4 centimeters in length and wound into a spiral about a glass rod. The cathode was a platinum wire having a diameter of 0.85 millimeters and a length of 24.5 centimeters also wound around a glass rod. The anode was located within the donor chamber and the cathode within the receiving chamber.

Doxorubicin hydrochloride, also known as adriamycin hydrochloride, was prepared in a saline solution to a concentration of 0.05 milligrams/milliliter. The solution was prepared by weighing 5.0 milligrams of doxorubicin hydrochloride and placing it into a 100 milliliter volumetric flask. About 50 milliliters of 0.9 percent NaCl solution was added to the flask which was then shaken well and sonicated for five minutes. The solution was then made up to 100 milliliter volume with additional 0.9 percent NaCl solution. The pH of this solution was 6.38 and the UV spectrum was measured using a Perkin-Elmer Lambda 3 UV/Visual Spectrophotometer at wavelengths of 494, 477, 265, 249, 230, and 202 nanometers. This spectrum was used as a reference to show the drug remained unchanged after it had passed through the membrane.

Using a pipette, 50 milliliters of the solution was placed within the donor chamber. As the study continued, additional solution was added from a reservoir to maintain the donor chamber level 3 centimeters above the receiving chamber level. The liquid level in the donor chamber was 3 centimeters higher than the level in the receiving chamber. The anode was connected to the positive pole and the cathode to the negative pole of a power supply which used a six volt battery. At first, the power was left off and a saline solution was passed through the receiving chamber at a flow rate of 100 milliliters per hour. The effluent was collected using a fraction collector programmed to collect up to a 50 milliliter sample every 30 minutes in separate test tubes. The effluent from the receiving chamber was collected for 24 hours and the presence of doxorubicin hydrochloride in the effluent was determined using high performance liquid chromatography (HPLC).

The chromatography column was a C18 du Pont Zorbax column 24 centimeters long, with a 4.6 millimeter internal diameter and a 10 micrometer particle size. The mobile phase was a 96.2 percent 2-propanol and 3.8 percent 0.5 moles/liter sodium acetate buffer with a pH of 4.5. The flow rate was 2.00 milliliters per minute at a pressure of 1600 pounds per square inch. The retention time of the doxorubicin hydrochloride peak was found to be 12.5 minutes.

The detector used was a Spectra Physics fixed wavelength detector set at a wavelength of 254 nanometers. A Valco Instrument Co. injector having a manual injection port with loop of 50 microliters was used with an L.D.C. HPLC pump.

A series of calibration solutions of this particular drug were prepared with concentrations of 0.1, 0.2, 0.5, 1.0, 2.0, 3.0, 5.0, 7.0, 8.0, 9.0, 10.0, 15.0 and 20.0 milligrams/milliliter. Each calibration solution was injected into the HPLC system and the corresponding peak area was obtained by a Spectra Physics SP 4100 integrator connected to the fixed wavelength detector. The plot of the peak area vs. concentration of calibration solution was used to calculate the concentration and therefore the amount of drug that had been delivered through the membrane. Peak area was found to be a linear function of concentration.

At the end of the 24 hour period with no current between the anode and the cathode, no doxorubicin was detected in the effluent. Therefore, the device does not allow the passage of therapeutic agent when there is no electromotive force between the electrodes.

After demonstrating that none of the drug passed through the membrane when the power was off, the power was then set at 6.00 volts and a current of 0.31 milliamps. A slight trace of doxorubicin could be seen in the receiving chamber because of its orange color. The HPLC chromatograms indicated that the effluent contained doxorubicin with the same retention time of 12.5 minutes as that of the starting material and that the ultraviolet and visible spectra also showed identical maximum peaks at 494, 477, 264, 269, 230, and 202 nanometers. This indicates there was no chemical change in the drug as it passed through the device.

Figure 4:
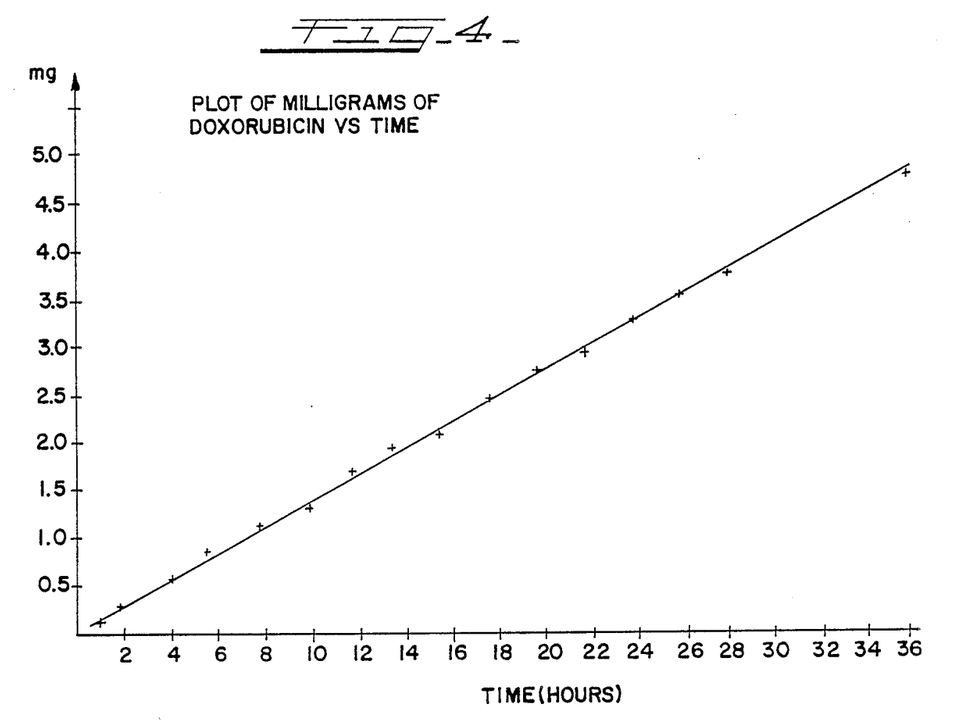
FIGS. 4–9 show results of studies of the present invention with the drugs doxorubicin hydrochloride, lidocaine hydrochloride, and clonidine hydrochloride.

The experiment was performed for 36 hours with four test tubes being pooled together to represent an average solution collected every two hours. The amount of the drug in milligrams was measured by the fixed wavelength detector and converted from curve area to milligrams by referring to the calibration curve described above. The results were plotted as a function of time and are shown in FIG. 4. As can be seen, the total amount of drug which had passed through the membrane by any given time was substantially linear with time for constant voltage and current.

Figure 5:
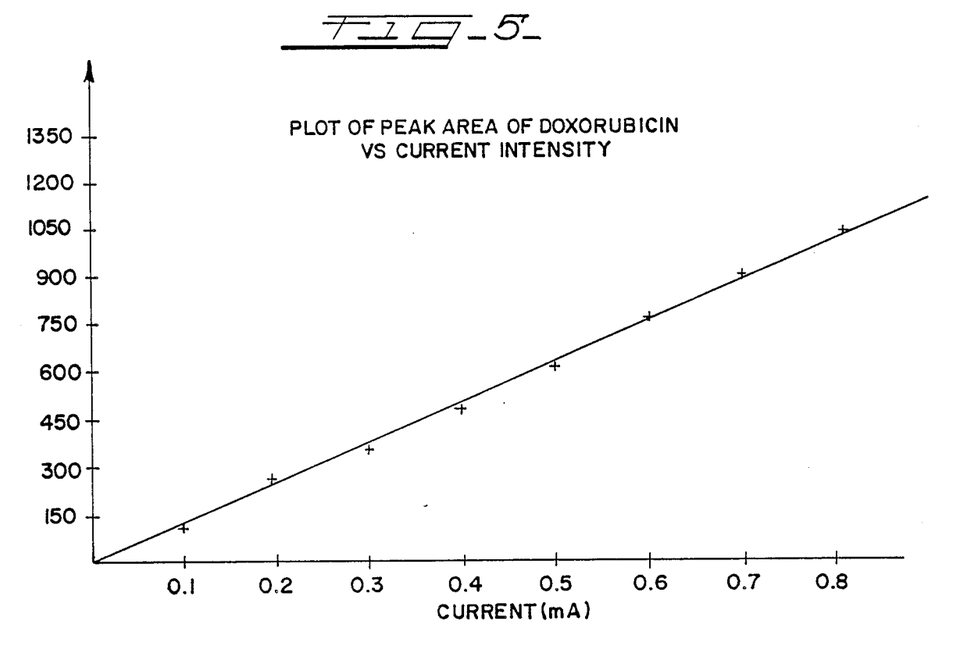

Next the delivery of the drug as a function of the current was examined. For each given current, the study was carried out for a period of two hours and the amount of doxorubicin hydrochloride was determined as described above. The results as measured by the peak area under each curve are plotted in FIG. 5. As can be seen from FIG. 5, the amount of drug released is directly proportional to the current between the anode and the cathode. This is a zero order profile. The slope of the lines shown in FIGS. 4 and 5 can be used as a standard calibration for doxorubicin and the particular membrane used. The slope, however, will be different for different drugs and different membranes.

EXAMPLE 2

The examinations of Example 1 were repeated except the drug lidocaine hydrochloride was prepared in a solution of 10 milligrams/milliliter using the same technique described above. The device and protocol used was the same as in Example 1.

The HPLC system was a Whatman C8 column, 15 centimeters long by 4.6 millimeter internal diameter. The mobile phase was 55 percent acetonitrile and 45 percent sodium acetate (0.10 moles/liter) solution having a pH of 4.5. The flow rate was 2.0 milliliters per minute at a pressure of 1200 pounds per square inch. The retention time of the lidocaine hydrochloride peak was found to be 8.5 minutes. UV spectroscopic measurements were made with the same equipment as in Example 1 at wavelength of 210.2 and 240.0 nanometers. The lidocaine hydrochloride in the effluent was checked using HPLC and the retention time and UV spectrum remained the same. Therefore, the drug did not undergo any change as it passed through the membrane.

Figure 6:
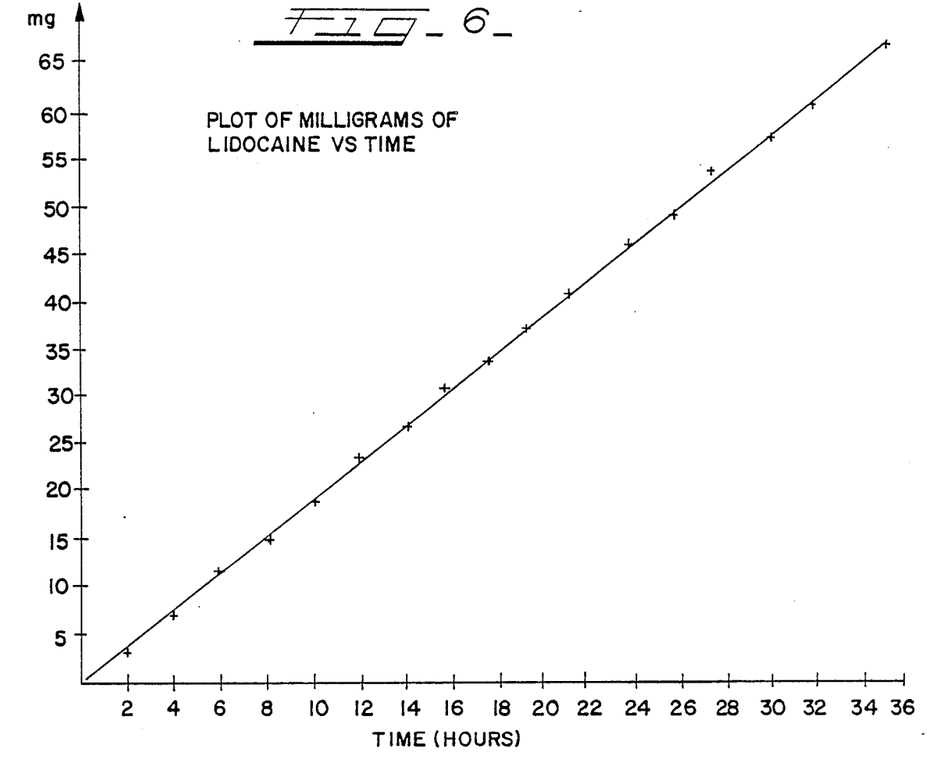

The amount of lidocaine hydrochloride in the effluent was measured using the fixed wavelength detector and integrator as in Example 1. A plot of peak area vs. concentration was similarly prepared. As can be seen by the results in FIG. 6, the amount of lidocaine hydrochloride passing through the membrane is a linear function of time with a constant voltage of 6.0 volts and current of 0.31 milliamps.

Figure 7:
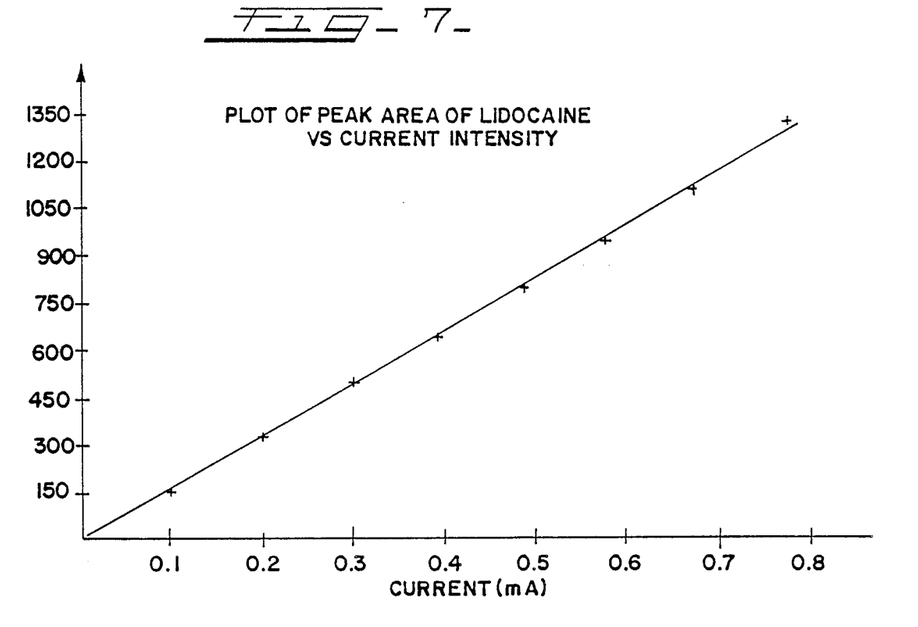

Similar to Example 1, the amount of lidocaine hydrochloride passing through the membrane as a function of current was also examined. As in Example 1, the test was for two hour periods for each current. The results as measured by the peak area output of the integrator are shown in FIG. 7. The delivery rate of lidocaine hydrochloride is thus also a linear function of the current.

EXAMPLE 3

This example examined the use of the device with the drug clonidine hydrochloride. A clonidine hydrochloride solution of 0.10 milligrams/milliliter was prepared using the same technique described above. The device and protocol used was the same as in Example 1.

HPLC column was the same as in Example 2. The mobile phase was 65 percent methanol and 35 percent sodium acetate buffer (0.10 moles/liter), pH 4.0. The flow rate was 2.0 milliliters per minute at a pressure of 1300 pounds per square inch. The retention time for clonidine hydrochloride peak was 5.7 minutes. UV spectroscopic measurements were made at wavelengths of 210 and 252 nanometers with the same equipment as in Example 1. The retention times and spectroscopic measurements remained the same after the drug passed through the membrane.

Figure 8:
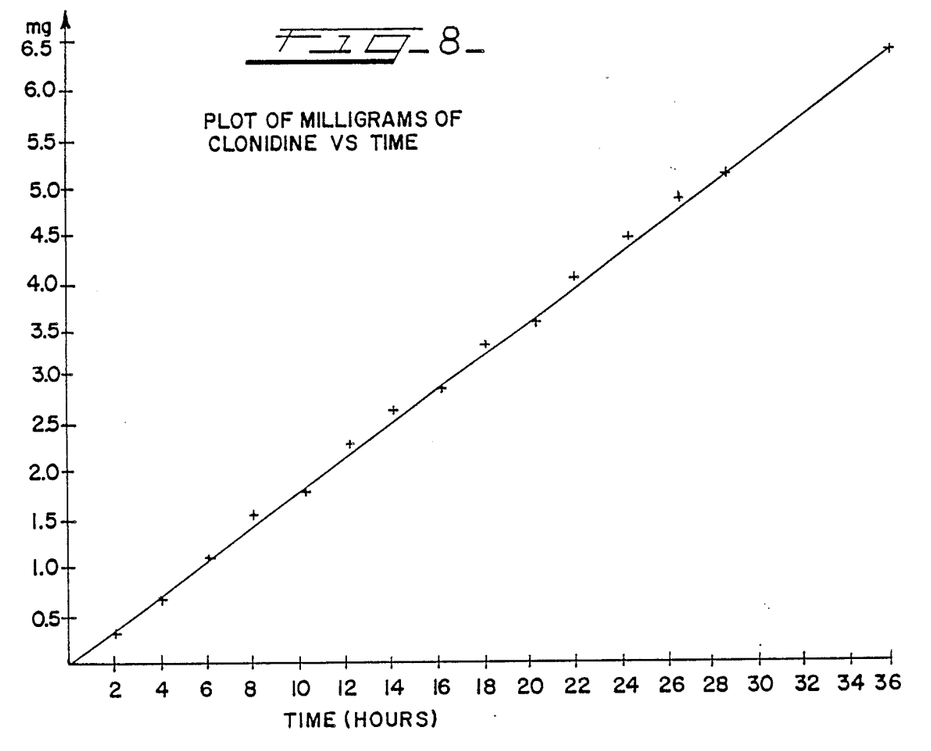

The amount of clonidine hydrochloride in the effluent was measured using the fixed wavelength detector and integrator as in Example 1. A plot of peak area vs. concentration was similarly prepared. As can be seen in FIG. 8, for a constant voltage of 6.0 volts and a current of 0.31 milliamps, the amount of clonidine hydrochloride in the effluent was a linear function with time.

Figure 9:
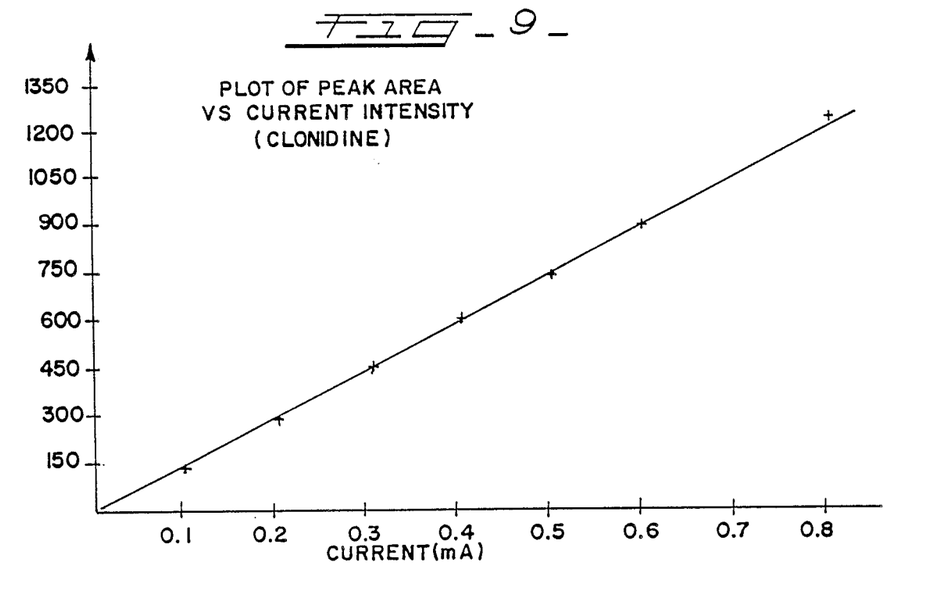

The amount of clonidine hydrochloride in the effluent as a function of current was measured by peak area as described above. As can be seen in FIG. 9, the amount of clonidine hydrochloride in the effluent for each two hour period was also a linear function of current.

As can be seen from the above examples, the amount and rate of therapeutic agent delivery is a linear function of time and current between the electrodes. This simplifies the controlled administration of the agent to the patient.

It will be understood that numerous other drugs or drug carrier systems can also be used as a therapeutic agent with the present invention.

What is claimed is:

1. A therapeutic agent delivery system comprising:
   a housing retaining a semipermeable membrane and together with the membrane defining a donor chamber adapted to hold the therapeutic agent, the membrane being made of a material that is substantially impermeable to the therapeutic agent in an ionic form;
   an anode and a cathode exposed within the donor chamber such that an electromotive force between the anode and the cathode will alter the electrical charge of the therapeutic agent to permit the agent to pass through the membrane.

2. The therapeutic agent delivery system of claim 1 including power source means for generating the electromotive force.

3. The therapeutic agent delivery system of claim 2 including control means for controlling the electromotive force generated by power source means over time.

4. The therapeutic agent delivery system of claim 3 wherein the system is adapted for implantation in a living body.

5. The therapeutic agent delivery system of claim 1 wherein the membrane is made of a hydrophobic material.

6. The therapeutic agent delivery system of claim 1 including a therapeutic agent received in the chamber in its ionic form.

* * * * *